(12) United States Patent
Wada et al.

(10) Patent No.: US 7,137,958 B2
(45) Date of Patent: Nov. 21, 2006

(54) HUMAN SPINAL COLUMN MEASUREMENT AND DISPLAY SYSTEM

(75) Inventors: Masaru Wada, Tokyo (JP); Sadao Omata, Tokyo (JP); Yoshikazu Kobayashi, Tokyo (JP); Kenji Shirai, Tokyo (JP)

(73) Assignee: Nihon University, Tokyo (JP)

( * ) Notice: Subject to any disclaimer, the term of this patent is extended or adjusted under 35 U.S.C. 154(b) by 139 days.

(21) Appl. No.: 10/487,243

(22) PCT Filed: Apr. 18, 2002

(86) PCT No.: PCT/JP02/03885

§ 371 (c)(1),
(2), (4) Date: Sep. 30, 2004

(87) PCT Pub. No.: WO03/017839

PCT Pub. Date: Mar. 6, 2003

(65) Prior Publication Data

US 2005/0020942 A1    Jan. 27, 2005

(30) Foreign Application Priority Data

Aug. 27, 2001  (JP) ............................. 2001-255547

(51) Int. Cl.
*A61B 5/103* (2006.01)
*A61B 5/117* (2006.01)

(52) U.S. Cl. ................. 600/594; 600/587; 600/595

(58) Field of Classification Search ............. 600/594, 600/416
See application file for complete search history.

(56) References Cited

U.S. PATENT DOCUMENTS

| | | | | |
|---|---|---|---|---|
| 4,760,851 A | * | 8/1988 | Fraser et al. ............... | 600/587 |
| 4,832,049 A | * | 5/1989 | Matsushita et al. .......... | 600/594 |
| 5,224,035 A | * | 6/1993 | Yamashita et al. .......... | 600/594 |
| 5,620,009 A | * | 4/1997 | DePasquale ................ | 600/594 |
| 6,480,735 B1 | * | 11/2002 | Colloca et al. ............. | 600/546 |
| 6,500,131 B1 | * | 12/2002 | Leitner et al. ............. | 600/594 |
| 2002/0133098 A1 | * | 9/2002 | Shechtman et al. ........ | 600/594 |
| 2003/0009099 A1 | * | 1/2003 | Lett et al. .................. | 600/416 |

FOREIGN PATENT DOCUMENTS

| | | |
|---|---|---|
| JP | 62-233146 | 10/1987 |
| JP | 63-35233 | 2/1988 |
| JP | 2000-93407 | 4/2000 |
| JP | 2000-245712 | 9/2000 |

* cited by examiner

*Primary Examiner*—Max F. Hindenburg
*Assistant Examiner*—Anuradha Roy
(74) *Attorney, Agent, or Firm*—Oblon, Spivak, McClelland, Maier & Neustadt, P.C.

(57) ABSTRACT

According to a human spinal column measuring and displaying system of the invention, a probe is pinched between the second finger and the third finger of a measuring person, front ends of the fingers are moved from the first thoracic vertebra to the fifth lumbar vertebra of the spinal column of a measured subject, detaching amounts from reference positions in X, Y and Z directions are detected by three-dimensionally moving the front ends of the fingers. Based on measured data, positions of displaying the vertebrae in correspondence with positions of coordinates in X direction, Y direction and Z direction of the respective vertebrae are moved and a three-dimensional image of the spinal column of the measured subject is generated and the image of the spinal column is displayed on a display screen.

2 Claims, 11 Drawing Sheets

(a) MEASURED VALUE OF MALE VERTEBRAE

| | BELLY SIDE HEIGHT AVERAGE VALUE ± STANDARD DEVIATION | BACK SIDE HEIGHT AVERAGE VALUE ± STANDARD DEVIATION | UPPER FACE ARROW SHAPE DIAMETER AVERAGE VALUE ± STANDARD DEVIATION | LOWER FACE ARROW SHAPE DIAMETER AVERAGE VALUE ± STANDARD DEVIATION | UPPER FACE LATERAL DIAMETER AVERAGE VALUE ± STANDARD DEVIATION | LOWER FACE LATERAL DIAMETER AVERAGE VALUE ± STANDARD DEVIATION |
|---|---|---|---|---|---|---|
| THIRD CERVICAL VERTEBRA (C3) | 12.93±1.45 | 12.39±1.41 | 15.23±0.93 | 16.41±1.41 | 20.44±1.38 | 20.60±2.47 |
| FOURTH CERVICAL VERTEBRA (C4) | 12.24±1.21 | 12.15±1.24 | 16.63±1.47 | 18.59±1.40 | 21.95±1.84 | 21.91±2.25 |
| FIFTH CERVICAL VERTEBRA (C5) | 11.42±1.19 | 11.76±1.18 | ........ | ........ | ........ | ........ |
| SIXTH CERVICAL VERTEBRA (C6) | 11.69±1.37 | 12.05±1.27 | | | | |
| SEVENTH CERVICAL VERTEBRA (C7) | 13.79±1.18 | 12.38±1.21 | | | | |
| ... | ... | ... | | | | |
| FIRST LUMBAR VERTEBRA (L1) | 23.39±1.80 | | | | | |
| SECOND LUMBAR VERTEBRA (L2) | 24.38±2.09 | | | | | |
| THIRD LUMBAR VERTEBRA (L3) | 24.81±1.82 | | | | | |
| FOURTH LUMBAR VERTEBRA (L4) | 24.89±2.02 | | | | | |
| FIFTH LUMBAR VERTEBRA (L5) | 25.15±2.29 | | | | | |

(b) MEASURED VALUE OF FEMALE VERTEBRAE

| | BELLY SIDE HEIGHT AVERAGE VALUE ± STANDARD DEVIATION | BACK SIDE HEIGHT AVERAGE VALUE ± STANDARD DEVIATION | UPPER FACE ARROW SHAPE DIAMETER AVERAGE VALUE ± STANDARD DEVIATION | LOWER FACE ARROW SHAPE DIAMETER AVERAGE VALUE ± STANDARD DEVIATION | UPPER FACE LATERAL DIAMETER AVERAGE VALUE ± STANDARD DEVIATION | LOWER FACE LATERAL DIAMETER AVERAGE VALUE ± STANDARD DEVIATION |
|---|---|---|---|---|---|---|
| THIRD CERVICAL VERTEBRA (C3) | 12.28±1.23 | 11.71±1.46 | 14.55±1.48 | 15.53±1.77 | 18.24±1.43 | 19.80±1.80 |
| FOURTH CERVICAL VERTEBRA (C4) | 11.61±1.17 | 11.30±1.42 | 14.98±1.59 | 15.46±1.69 | 20.81±1.76 | 20.66±2.11 |
| FIFTH CERVICAL VERTEBRA (C5) | 11.36±1.53 | 11.61±1.57 | ........ | ........ | ........ | ........ |
| SIXTH CERVICAL VERTEBRA (C6) | 11.43±1.33 | 11.59±1.50 | | | | |
| SEVENTH CERVICAL VERTEBRA (C7) | 13.22±1.19 | 12.83±1.23 | | | | |
| ... | ... | ... | | | | |
| FIRST LUMBAR VERTEBRA (L1) | 23.78±1.94 | | | | | |
| SECOND LUMBAR VERTEBRA (L2) | 24.66±2.00 | | | | | |
| THIRD LUMBAR VERTEBRA (L3) | 24.69±2.22 | | | | | |
| FOURTH LUMBAR VERTEBRA (L4) | 24.59±2.09 | | | | | |
| FIFTH LUMBAR VERTEBRA (L5) | 25.85±2.11 | | | | | |

HUMAN SPINAL COLUMN MEASUREMENT AND DISPLAY SYSTEM

TECHNICAL FIELD

The present invention relates to a human spinal column measuring and displaying system capable of measuring bending of the spinal column of the human body by a simple and convenient method and capable of displaying the spinal column on a display screen in a real mode based on a measured value thereof.

BACKGROUND ART

It has conventionally been known that warping or bending of the spinal column effects various influences such as diseases of the internal organs, the stiffness in the shoulder and the head ache on the human body. Therefore, in order to confirm whether bending is present at the spinal column, there are used a manual method of confirming whether the spinal column is bent by examining the spinal column position of the human body by touching by a physician of the chiropractic, a method of using Moire topography capable of optically recognizing whether a Moire pattern symmetrical in left and right direction is described on the surface of the human body and a method of using thermography capable of detecting temperature of the surface of the human body caused by a failure in blood flow and optically recognizing warping of the body (bending of the spinal column) by a distribution of the temperature.

Further, when it is found that bending is present at the spinal column, an image of the Moire topography or the thermography is made to be seen by a patient and an explanation stating 'the spinal column is bent to the right or to the left' is given from a surface state of the human body. Further, in diagnosis by touching, an explanation is orally given to a patient of a result of the diagnosis by touching.

Further, a predetermined treatment is carried out from the surface of the human body to the bent spinal column by manual therapy by the physician to thereby correct or improve the bending of the spinal column.

However, according to the above-described background art method, in explaining a state of the spinal column given to the patient (measured subject), only the oral explanation is given to the patient and therefore, a specific bent state of the spinal column cannot be known. Further, in order to know a specific degree of the bending of the spinal column from a display content of the image of the Moire topography or the thermography, skill is required to grasp the display content and it is difficult to know the bent degree of the spinal column simply by a nonprofessional person. Further, even when the bent spinal column is diagnosed by touching and thereafter, a result of carrying out the predetermined treatment is explained, the diagnosis by touching or the treatment per se is much dependent on the technique and the experience of the physician and for the patient (measured subject), even when the degree of bending of the spinal column of one's own or the degree of correcting the spinal column is explained, it is difficult to understand the specific state of the bending such as how much which portion of the spinal column is bent in which direction, or how much the bending of the spinal column is corrected after the treatment. That is, in explaining orally of the bent state of the spinal column by the physician, a specialized expression is given such that, for example, 'number XX of the superior thoracic vertebrae becomes so and so.' and there poses a problem that it is difficult to understand how which of the thoracic vertebrae of one's own is bent.

DISCLOSURE OF THE INVENTION

The invention has been carried out in view of the above-described situation of the background art and it is an object thereof to provide a human spinal column measuring and displaying system capable of calculating a measured data of three-dimensional coordinates of the spinal column by scanning a predetermined probe along the spinal column, simulating a shape of the spinal column from the measured data and displaying a three-dimensional pseudo-image of the spinal column by utilizing computer graphics.

The invention according to Claim 1 relates to a human spinal column measuring and displaying system characterized in comprising a probe provided at a front end of a scanning arm movable in a longitudinal direction (X-axis direction), a width direction (Y-axis direction) and a thickness direction (Z-axis direction) of the spinal column of a measured subject and pinched between the second finger and the third finger of a measuring person for detecting detaching amounts from reference positions in the X, the Y and the Z directions by three-dimensionally moving front ends of the fingers by moving the front ends of the fingers from a position of the first cervical vertebra or a position of the first thoracic vertebra to a position of the fifth lumbar vertebra of the spinal column of the measured subject, converted data storing means for storing respective values of measured data in the X-axis direction, the Y-axis direction and the Z-axis direction of the detaching amounts detected by the probe, an input apparatus for inputting the gender and the height of the measured subject, a basic diagram data stored with an average size and a basic shape of each of the vertebrae constituting the spinal column of the human body by the gender and the height of the measured subject, a table of the vertebrae for selecting each of the vertebrae in correspondence with the gender and the height from the basic diagram data in accordance with the gender and the height of the measured subject inputted by the input apparatus, synthesizing means for generating an image of a total of the spinal column constituting a basic based on a size and a shape of each of the vertebrae selected by the table of the vertebrae, and image data generating means for generating a three-dimensional image of the spinal column of the measured subject at positions of coordinates in the X direction, the Y direction and the Z direction of each of the vertebrae on the image of the spinal column generated by the synthesizing means based on the measured data stored to the converted data storing means to display the image of the spinal column on a display screen.

The invention according to Claim 2 relates to the human spinal column measuring and displaying system according to Claim 1, characterized in that the pseudo-image of the spinal column is displayed by moving the image of the spinal column displayed on the display screen in a predetermined direction or rotating the image by a predetermined angle based on a predetermined instruction.

BRIEF DESCRIPTION OF THE DRAWINGS

FIG. 6 illustrates explanatory views of a table of the vertebrae of the human spinal column measuring and displaying system according to the embodiment of the invention.

BEST MODE FOR CARRYING OUT THE INVENTION

An explanation will be given of an embodiment of the invention in reference to the drawings as follows.

Figure 1:
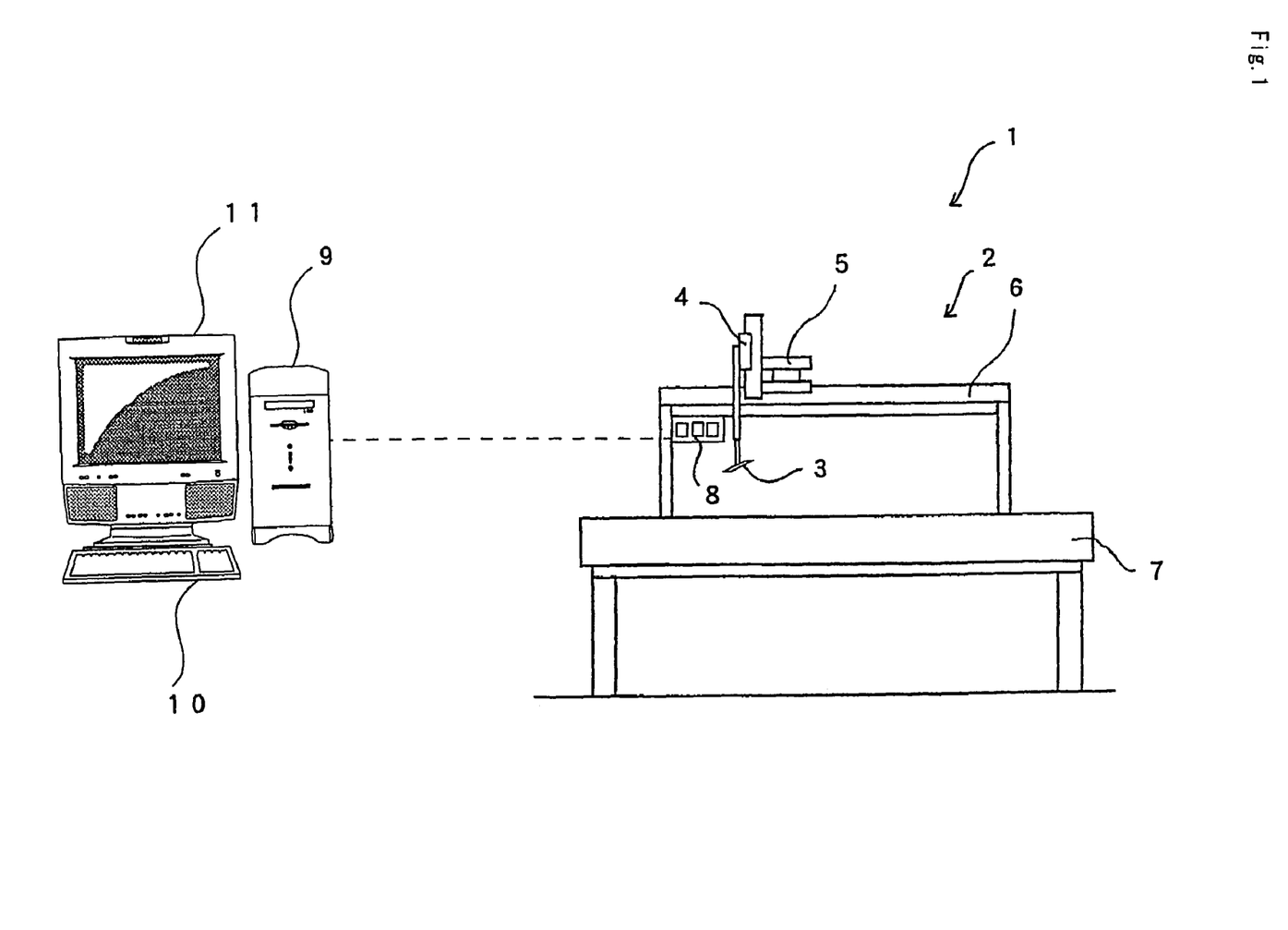
FIG. 1 is an outline constitution view of a human spinal column measuring and displaying system according to an embodiment of the invention.

FIG. 1 is an outline constitution view of a human spinal column measuring and displaying system according to the invention. In FIG. 1, numeral 1 designates a human spinal column measuring and displaying system, numeral 2 designates a spinal column measuring apparatus, numeral 3 designates a probe for scanning the spinal column from the surface of the human body, numeral 4 designates a vertical support arm, numeral 5 designates a parallel support arm, numeral 6 designates a measuring direction support arm (a scanning arm is constituted by the vertical support arm 4, the parallel support arm 5 and the measuring direction support arm 6), numeral 7 designates a measuring couch, numeral 8 designates a coordinates detecting apparatus, numeral 9 designates a display apparatus main body, numeral 10 designates an output apparatus and numeral 11 designates a display screen.

The probe 3 is for scanning the spinal column of the patient (measured subject) from above the surface, a shape thereof is constituted by an inverse T-like shape and a bottom portion thereof is constituted by a slightly recessed shape to be in line with recesses and projections of the spinal column. Further, according to the embodiment, the probe 3 includes a sensor (a magnetic scale type digital sensor).

That is, the probe 3 is pinched between the second finger and the third finger of a measuring person and front ends of the second finger and the third finger are brought into contact with a measured subject to move along the spinal column from a position of the first cervical vertebra or a position of the first thoracic vertebra (the root of the neck) to a position of the fifth lumbar vertebra of the spinal column of the measured subject to measure the bent state of the spinal column by a moving amount (detaching amount) thereof.

The vertical support arm 4 is provided with the probe 3 at a lower front end thereof and is provided to be movable along recesses of projections of the spinal column in a thickness direction of the breast (Z-axis direction).

The parallel support arm 5 is provided with the vertical support arm 4 provided with the probe 3 to be movable in a width direction of the back (Y-axis direction).

The measuring direction support arm 6 is provided with the parallel support arm 5 movably in a longitudinal direction of the spinal column (X-axis direction) and is provided at one side portion of the measuring couch 7 in line with a longitudinal direction thereof.

The measuring couch 7 is constituted by a size of a width of about 600 mm, a length of about 1800 mm and a height of about 500 mm by which the patient (measured subject) can lie on one's head. The measuring couch 7 is for accurately measuring the spinal column when the spinal column of the patient (measured subject) is brought into a constant state by letting the patient (measured subject) lie on one's face at a predetermined position of the measuring couch 7 and the probe 3 is scanned above the spinal column.

That is, the measuring couch 7 is constituted such that in measuring the bent state of the spinal column of the patient (measured subject) lying on the measuring couch 7, when the measuring person holds the probe 3 by the hand to move from the neck in the direction of the waist above the surface of the spinal column, the probe 3 follows recesses and projections and shifts in left and right direction by the vertical support arm 4, the parallel support arm 5 and measuring direction support arm 6 within a range of, for example, 900 mm in X direction, 400 mm in Y direction and 200 mm in Z direction.

According to the embodiment, the coordinates detecting apparatus 8 is attached to the measuring direction support arm 6 and counts moving amounts in X direction, Y direction and Z direction of the probe 3 as predetermined pulse signals by, for example, an encoder (24 bits up and down counter board (PCN24-4 (PCI))) and detects coordinate values and digital values when the coordinate values coincide with count comparison values arbitrarily set for the respective coordinates. Further, detected measured data is transmitted to the display apparatus main body 9.

Figure 2:
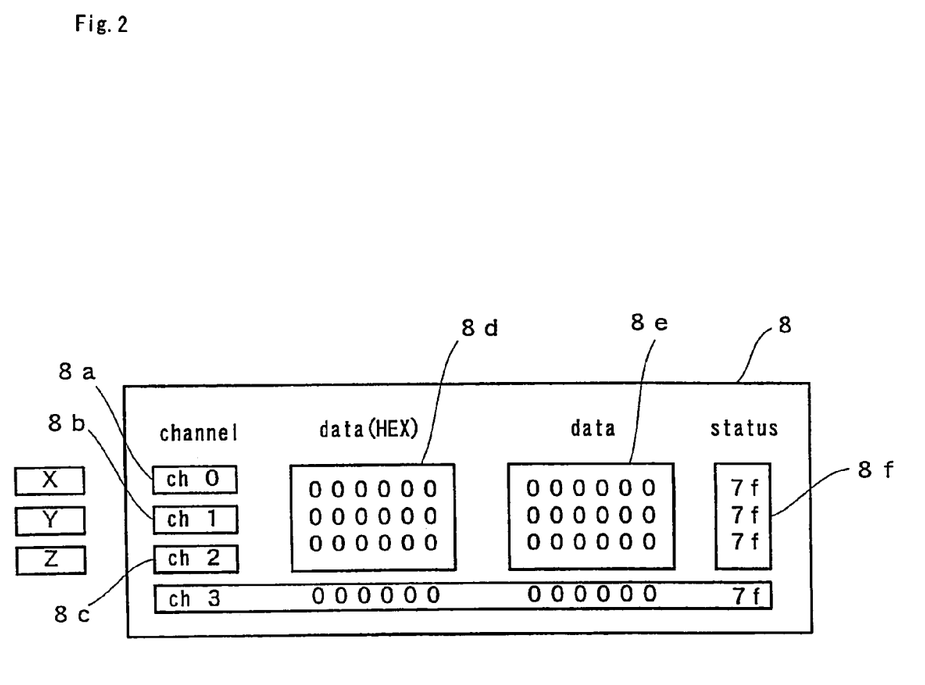
FIG. 2 is an explanatory view of a coordinates detecting system of the human spinal column measuring and displaying system according to the embodiment of the invention.

FIG. 2 is an explanatory view of the coordinates detecting apparatus 8 and the coordinates detecting apparatus 8 includes respective channels (ch0, ch1, ch2) 8a, 8b and 8c of X-coordinate axis, Y-coordinate axis and Z-coordinate axis, a hexadecimal display portion 8d for detecting and displaying hexadecimal data, a decimal display portion 8e for detecting and displaying decimal data and a status 8f for detecting and displaying counts of coordinates values at each 0.1 second.

Figure 3:
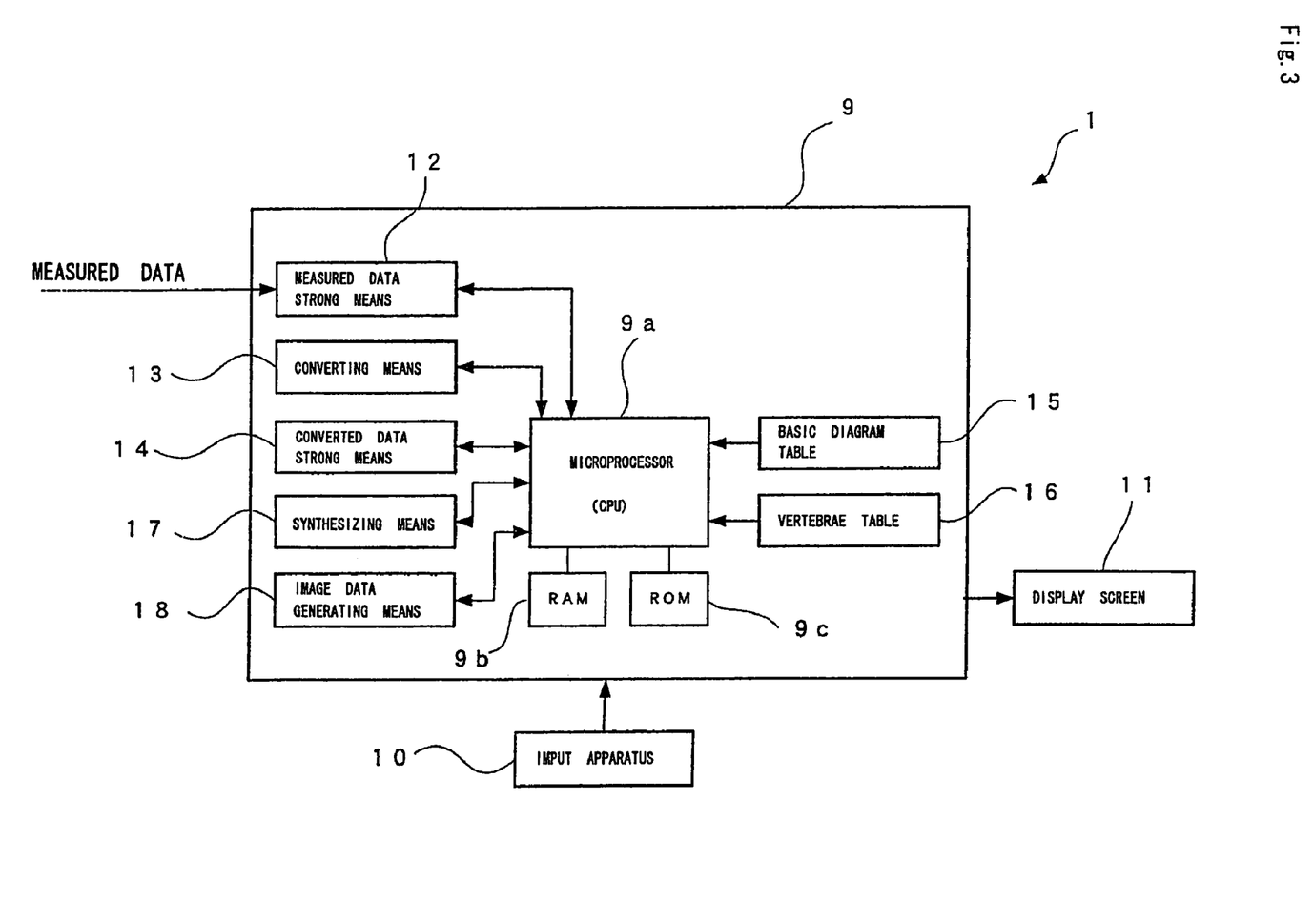
FIG. 3 is a block diagram of the display apparatus main body of the human spinal column measuring and displaying system according to the embodiment of the invention.

FIG. 3 is a block diagram of the display apparatus main body 9 for displaying the bent state of the spinal column and is connected with the input apparatus 10 and the display screen 11.

In FIG. 3, numeral 12 designates measured data storing means for storing a measured data of a digital value converted by the coordinates detecting apparatus 8, numeral 13 designates converting means for converting the measured data stored to the measured data storing means 12 by a predetermined conversion procedure, numeral 14 designates converted data storing means for storing a converted data converted by the converting means 13, numeral 15 designates basic diagram data stored with image data of a basic model of the vertebrae, numeral 16 designates data of a table of the vertebrae which is referred to when a spinal column image is formed by the converted data, numeral 17 designates synthesizing means for forming an image of the vertebrae of the measured subject based on the converted data and numeral 18 designates image data generating means for generating the respective vertebrae formed by the synthesizing means 17 for the spinal column.

According to the embodiment, the display apparatus main body 9 is, for example, a personal computer executing predetermined operation based on the measured data transmitted from the spinal column measuring apparatus 2 and forming an image data displaying the state of the spinal column in real mode.

For example, according to the embodiment, as a personal computer, PowerMac 7100/66AV of Apple corporation is used and as a microprocessor 9a having ROM9b and RAM9c constituting storing means, PowerPC601 of 66 MHz is mounted. Further, an image processing is carried out by an image processing software program of three-dimensional computer graphics (for example, Adobe Premire 3.0) executed by the microprocessor 9a.

The input apparatus 10 is a keyboard or a mouse connected to the display apparatus main body 9 for inputting information of a height or the like of the measured subject of the spinal column.

The display screen 11 is a CRT display screen or a liquid crystal display screen for displaying the measured state of the spinal column by an image in a real mode.

The measured data storing means 17 is stored with a digital measured data transmitted from the coordinates detecting apparatus 8 as coordinate values in X direction, Y direction and Z direction.

The converting means 13 is for converting the measured data stored in the measured data storing means 17 into the converted data by a predetermined method.

The converted data storing means 14 is stored with a result of converting the measured value by the converting means 13 as the converted data.

That is, the X-axis direction is constituted by a moving direction of the measuring and scanning means 3 from the head to the waist of the human body along the frame 2b, the Y-axis direction is constituted by a direction of moving the measuring and scanning means 3 in up and down direction along recesses and projections of the spinal column of the human body and the Z-axis direction is constituted by a moving directions of the measuring and scanning means 3 in the width directions of the human body along 'bending' or the like of the spinal column of the human body.

Figure 4:
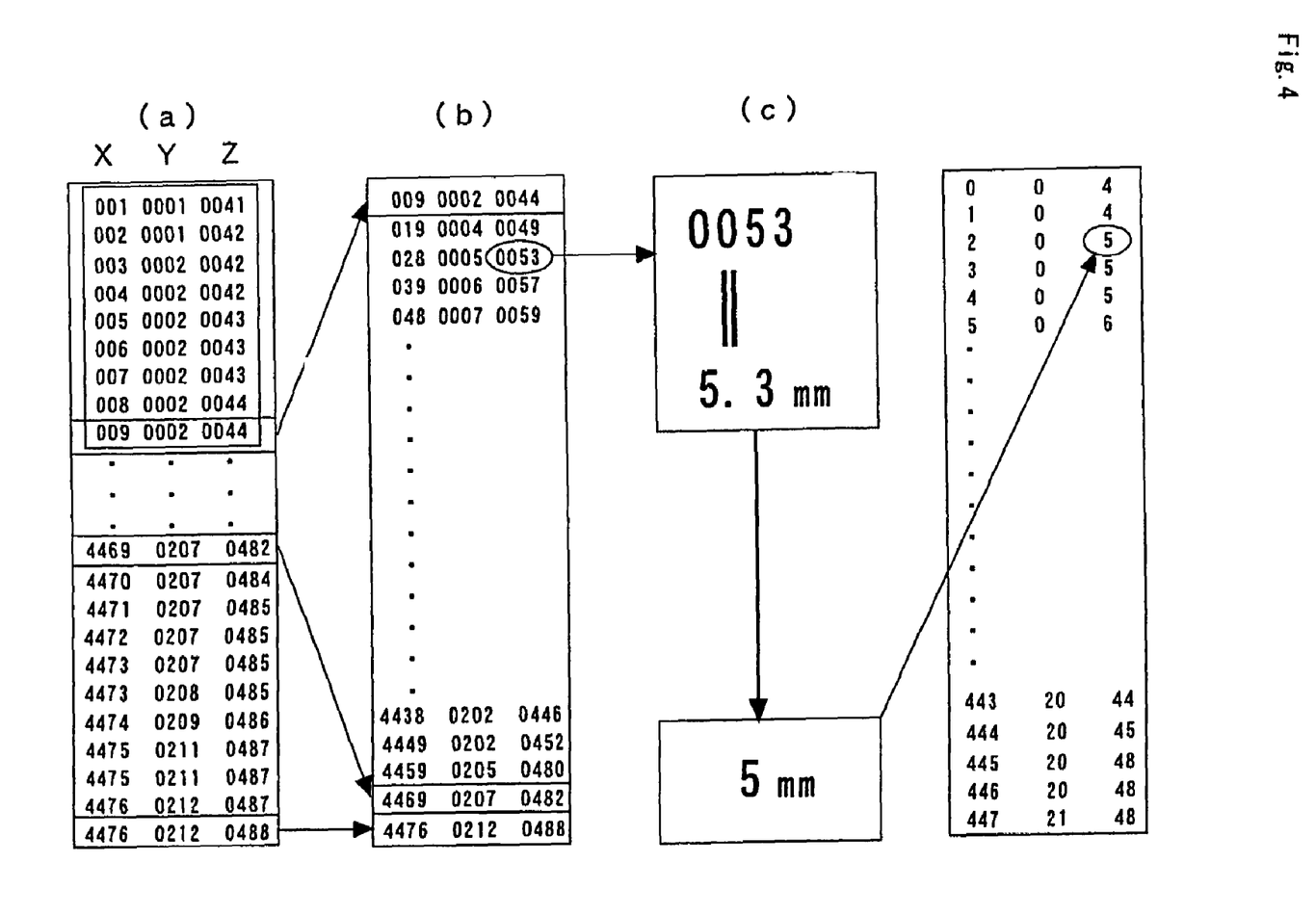
FIG. 4 illustrates explanatory views of a behavior of converting a measure data into a converted data by converting means of the human spinal column measuring and displaying system according to the embodiment of the invention.

FIG. 4 illustrates explanatory views of a behavior of converting the measured data into a converted data by the converting means 13.

That is, FIG. 4 (a) is the measured data stored to the measured data storing means 12 and is the measured data respectively in X direction, Y direction and Z direction from left. By dividing X direction (length direction of the spinal column) for each 1 mm by the converting means 13, there are detected '009' which is a maximum coordinate value in X direction from '001' to '009', '019' which is a maximum thereof from '011' to '019', . . . , '4469' which is a maximum thereof from '4461' to '4469' and a final data '4476', that is, values in X direction of '009', '019', . . . , '4469', '4476' and the coordinate values in X direction, Y direction and Z direction are temporally stored to a memory (RAM or the like) (refer to FIG. 4(b)).

The measured data detected in this way is a numerical value a lower first number of which is equal to or smaller than a decimal point and since an error in measurement is conceivable to include, an integer is provided by rounding down numbers below the decimal point.

Further, as shown by FIG. 4(b), a coordinate value in X direction, a coordinate value in Y direction and a coordinate value in Z direction constituting an initial measured data is (X, Y, Z)=(009, 0002, 0044) and when numbers below the decimal point of the measured data are rounded down, (X, Y, Z)=(0, 0, 4) Next, (X, Y, Z)=(019, 0004, 0049) becomes (X, Y, Z)=(1, 0, 4) successively, (X, Y, Z)=(029, 0005, 0053) becomes (X, Y, Z)=(2, 0, 5) and a final measure data (X, Y, Z)=(4476, 0212, 0488) becomes (X, Y, Z)=(447, 21, 48) which are respective values respectively converted into integers (refer to FIG. 4(c)).

Further, the converted respective values are stored to the converted data storing means 14 as converted data based on the measured data.

Next, since a number of the vertebrae constituting the spinal column of the human body is determined, the length of the spinal column is changed by a height difference or the like. Hence, an average measured value data constituting the base is previously stored as the vertebrae table 16. Further, when the shape of the vertebrae is stored to the basic diagram data 15 as a basic model and a simulation of the spinal column of the measured subject is carried out by reflecting the converted data based on the measured value to the vertebrae table 16 and the basic diagram data 15, a pseudo-spinal column can be displayed as an image in a real mode and, for example, it can be known which vertebra is a portion at which the spinal column is bent.

The basic diagram data 15 is an image data of shapes of the vertebrae comprising the cervical vertebrae (7 pieces), the thoracic vertebrae (12 pieces), the lumbar vertebrae (5 pieces), the sacral vertebrae (5 pieces) and coccygeal vertebrae (5 pieces). As the basic structure of the vertebrae, the vertebrae are contiguous to each other in up and down direction by interposing the intervertebral disks on the berry side, having clearances (the vertebra holes) passing the spiral cord and surrounded by the bones on the back side and having thorn projections on the rear side.

Figure 5:
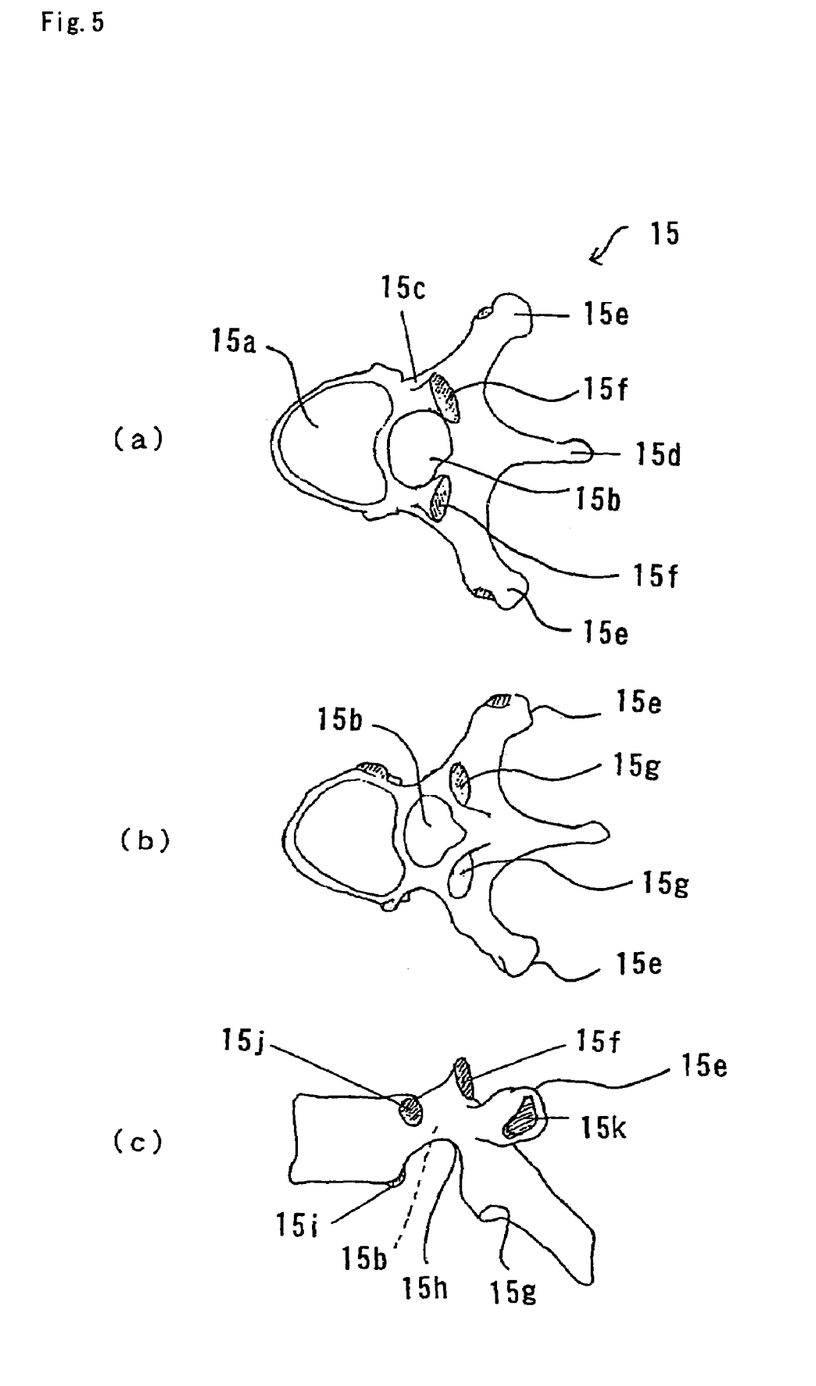
FIG. 5 illustrates explanatory views of a basic structure of the vertebra (the fourth thoracic vertebra) constituting the spinal column (the vertebrae) displayed by the human spinal column measuring and displaying system according to the embodiment of the invention.

FIG. 5 illustrates explanatory views of the basic structure of the vertebra (the fourth thoracic vertebra) constituting the spinal column (spine).

FIG. 5 (a) is a shape of an upper face of the vertebra 15 comprising by respectively forming the vertebra body 15a which is rounded, the vertebra hole 15b on the back side, the lamina roots 15c on both side portions of the vertebra hole, the thorn projection 15d at the center of the backside and the lateral projections 15e at both side portions thereof and forming the upper joint projections 15f continuous to other vertebra on skewed upper sides (back side direction) on both side portions of the vertebra hole 15b.

FIG. 5 (b) shows a shape of a lower face of the vertebra 15 and constituted by forming the lower joint projections 15b continuous to other vertebra on skewed lower sides (directions from the back side to the berry side) on both side portions of the vertebra hole 15b.

FIG. 5 (c) shows a shape of a left side face of the vertebra 15 which is formed by the lower vertebra cut marks 15h chipped off in a semicircular shape on the lower side of the vertebra hole 15b, lower rib cavities 15i on both lower sides on the berry side of the lower vertebra cutting marks 15h, the upper rib cavities 15j on both upper sides of the lower rib cavities and the laterally projected rib cavities 15k at front end portions of the lateral projections 15e.

Further, the image data of the respective vertebrae constituting such shapes are stored to the basic diagram data 15.

According to the embodiment, the vertebrae table 16 is constituted by tabulating, for example, average measured values (±standard deviations) of the vertebrae of a Japanese adult male person and average measured values (±standard deviations) of the vertebrae of a Japanese adult female person.

FIG. 6 shows the average measured values of the vertebrae as the vertebrae table 16, FIG. 6(a) shows measured values of the vertebrae of a Japanese adult female person (age : 26 years), for example, average values (±standard deviations) of berry side heights thereof are 12.93 mm±1.45 mm for the third cervical vertebra, 12.24 mm±1.21 mm for the fourth cervical vertebra, . . . , 15.12 mm±1.12 mm for the first thoracic vertebra, . . . , 22.33 mm±1.91 mm for the twelfth thoracic vertebra, 23.39 mm±1.80 mm for the first lumbar vertebra, . . . , 25.15 mm±2.29 mm for the fifth lumbar vertebra, showing respectives of back side heights, upper face arrow shape diameters, lower face arrow shape diameters, upper face lateral diameters and lower face lateral diameters for the third cervical vertebra through the fifth lumbar vertebra.

FIG. 6 (b) shows average measured values of the vertebrae of a Japanese adult female person (age : 26 years), similarly, average values (±standard deviations) of berry side heights are 12.28 mm±1.23 mm for the third cervical vertebra, 11.61 mm±1.17 mm for the fourth cervical vertebra, , 14.89 mm±1.23 mm for the first thoracic vertebra, , 22.10 mm±1.8 mm for the twelfth thoracic vertebra, 23.76 mm±1.94 mm for the first thoracic vertebra, , 24.85 mm±2.11 mm for the fifth lumbar vertebra, showing respectives of back side heights, upper face arrow shape diameters, upper face lateral diameters, and lower face lateral diameters for the third cervical vertebra through the fifth lumbar vertebra.

Further, the vertebrae tables 16 are formed and stored for respective male and female persons.

The synthesizing means 17 provides a pseudo-image of the spinal column in a real mode by reflecting sizes in accordance with the vertebrae table 16 to images of shapes of the respective vertebrae stored to the basic diagram data 15. That is, among the respective vertebrae stored to the basic diagram data 15, for example, the third thoracic vertebra is disposed on the upper side of the fourth thoracic vertebra by interposing the intervertebral disk and the upper joint projection 15f of the fourth thoracic vertebra and the lower joint projection 15g of the third thoracic vertebra are continuous to each other. Further, when the first cervical vertebra through the coccyx are successively synthesized such that the second thoracic vertebra is disposed on the upper side of the third thoracic vertebra and the first thoracic vertebra is disposed on the upper side, the image of the spinal column is formed.

That is, the data stored to the vertebrae table 16 is constituted by average values of Japanese taking into account standard deviations and based on the gender and height, by sizes of 17 pieces of the vertebrae from the first thoracic vertebra at start of measurement through the fifth lumbar vertebra (actual display is 24 pieces of the first cervical vertebra through the fifth lumbar vertebra), the basic diagram data 15 is selected to combine to provide the image of the spinal column of the basic model.

According to the embodiment, the image data generating means 18 generates an image data of a state of the spinal column of the individual measured subject by reflecting the converted data (measured data) to the shape of the spinal column constituting the basic formed by the synthesizing means 17.

That is, as described above, in the converted data (measured data), for each 1 mm in X direction which is the longitudinal direction of the spinal column, positions in Y direction which is the width direction of the back and Z direction which is the thickness direction of the breast are measured and the converted data (measured data) are divided to allocate to the respective vertebrae. Then, it is determined that what mm to what mm of X values correspond to 'the number×lumbar vertebra'.

Further, the image data of the spinal column can be displayed by rotating the image of the spinal column in a predetermined direction when the coordinates of the view point are changed by utilizing the above-described image processing software program of the three-dimensional computer graphics executed by the microprocessor 9a.

Figure 7:
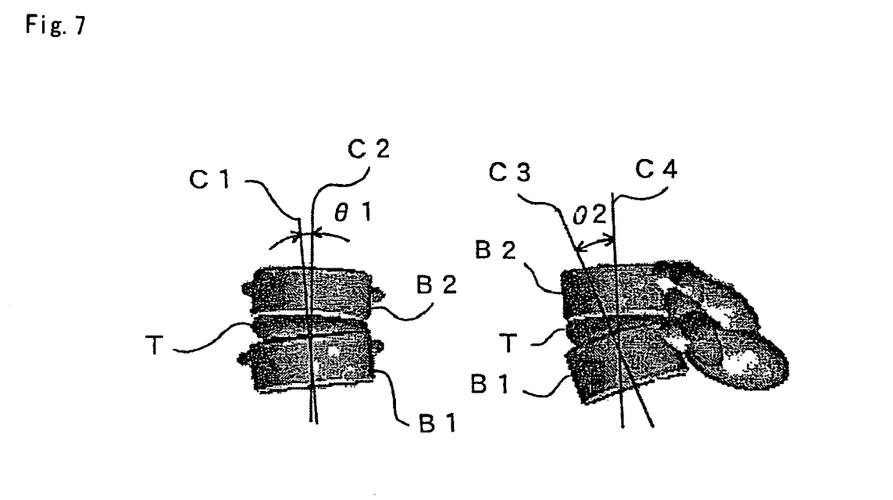
FIG. 7 is an explanatory view showing a behavior of calculating an angle between the vertebrae of the human spinal column measuring and displaying system according to the embodiment of the invention.

FIG. 7 illustrates explanatory views showing a behavior of calculating angles among the vertebrae, FIG. 7 (a) is an explanatory view showing a bent angle in left and right direction between the vertebrae and FIG. 7 (b) is an explanatory view showing a bent angle in front and back directions there between.

When as shown by FIG. 7 (a), for example, the third lumbar vertebra is designated by notation B1, the intervertebral disk is designated by notation T and the second lumbar vertebra is designated by notation B2, the bent angle can be calculated from Y value in correspondence with the portion of the second lumbar vertebra and Y value in correspondence with the portion of the third lumbar vertebra of the converted data (measure data) divided into the respective vertebrae. That is, when the spinal column is not bent, since the spinal column is not inclined to either of left and right and therefore, all of Y values become '0', further, for example, when the second lumbar vertebra is inclined to right, Y value is measured as '1' or '2' and when the second lumbar vertebra is inclined to left, Y value is measured as '−1' or '−2'.

When the converted data (measure data) is reflected to the basic model of the spinal column, it is calculated that there is brought about an inclination of an amount of an angle θ1 between center C1 of the third lumbar vertebra and center C2 of the second lumbar vertebra and the image of the vertebrae is generated by deforming the intervertebral disks T.

Next, when as shown by FIG. 7 (b), similar to the above-described, the third lumbar vertebra is designated by notation B1 and the second lumbar vertebra is designated by notation B2, the image of the vertebrae can be provided from Z value in correspondence with the portion of the second lumbar vertebra and Z value in correspondence with the portion of the third lumbar vertebra of the converted data (measured data) divided to the respective vertebrae.

That is, in the case of the lumbar vertebrae, when there the second lumbar vertebra (C4) is inclined relative to the third lumbar vertebra (C3) to the back side by '9.27 degrees' in the basic model in which Z value is '−10'(according to the embodiment, with respect to a plane comprising X coordinates and Y coordinates, this side is indicated as plus and depth side is indicated as minas), is normal and in contact thereto, when Z value of the converted data (measured data) is '−7', an inclination θ2 between C3 and C4 is calculated as, for example, '5.06 degrees'.

By providing inclinations provided in this way to the spinal column image of the basic model, the original state of the spinal column based on the gender and height of the measured subject is generated as image data.

Further, the provided image data is displayed as a pseudo-image of the spinal column on the display screen 11 connected to the display apparatus main body (personal computer) 9 by utilizing the three-dimensional computer graphics.

Figure 8:
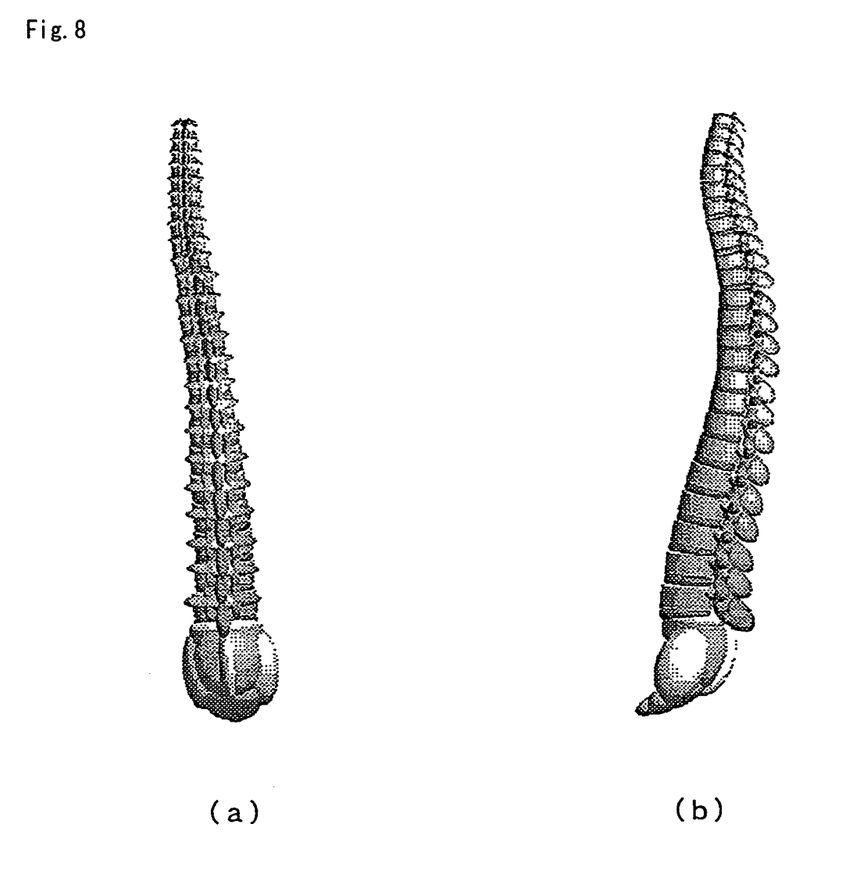
FIG. 8 illustrates explanatory views of images of the spinal column displayed on a display screen of the human spinal column measuring and displaying system according to the embodiment of the invention.

FIG. 8 illustrates images of the spinal column generated by measuring the spinal column by the human spinal column measuring and displaying system 1 and based on the measured data.

FIG. 8 (a) shows an image of the spinal column on the backside generating a total of the measured spinal column and displaying the spinal column from the back side and FIG. 1 (b) shows an image of the spinal column on the left side generating the total of the measured spinal column and displaying the spinal column on the left side.

As shown by FIG. 8 (a), the total of the spinal column is divided into the cervical vertebrae portion, the superior thoracic vertebrae, the middle thoracic vertebrae, the inferior thoracic vertebrae, the lumbar vertebrae, the sacral vertebrae and the coccygeal vertebrae and displayed respectively by being classified by colors according to the embodiment. For example, by displaying to classify by colors such that the cervical brae is 'white' the superior thoracic vertebrae is 'red', the middle thoracic vertebrae is 'blue', the inferior thoracic vertebrae is 'green', the lumbar vertebrae is 'yellow' and the sacral vertebrae and the coccygeal vertebrae are 'gray', it can easily be recognized optically where is the portion at which the spinal column is bent and in which direction the spinal column is bent. Further, since the image data for displaying the spinal column is image data of the three-dimensional computer graphics, an image of the spinal column in which the coordinates of the view point are changed by the image data generating means 18 and the image of the spinal column on the left side as shown by FIG. 8 (b) can be displayed.

Further, when it is considered that, for example, 'bending of the superior thoracic vertebrae is abnormal', only the superior thoracic vertebrae can be displayed.

In a state in which the images of FIG. 8 (a) and FIG. 8 (b) are displayed, by depressing predetermined keys (for example, 'UP key (↑)' or 'DOWN key (↓)') provided at the input apparatus 10, the display can be switched to display of only the superior thoracic vertebrae.

Figure 9:
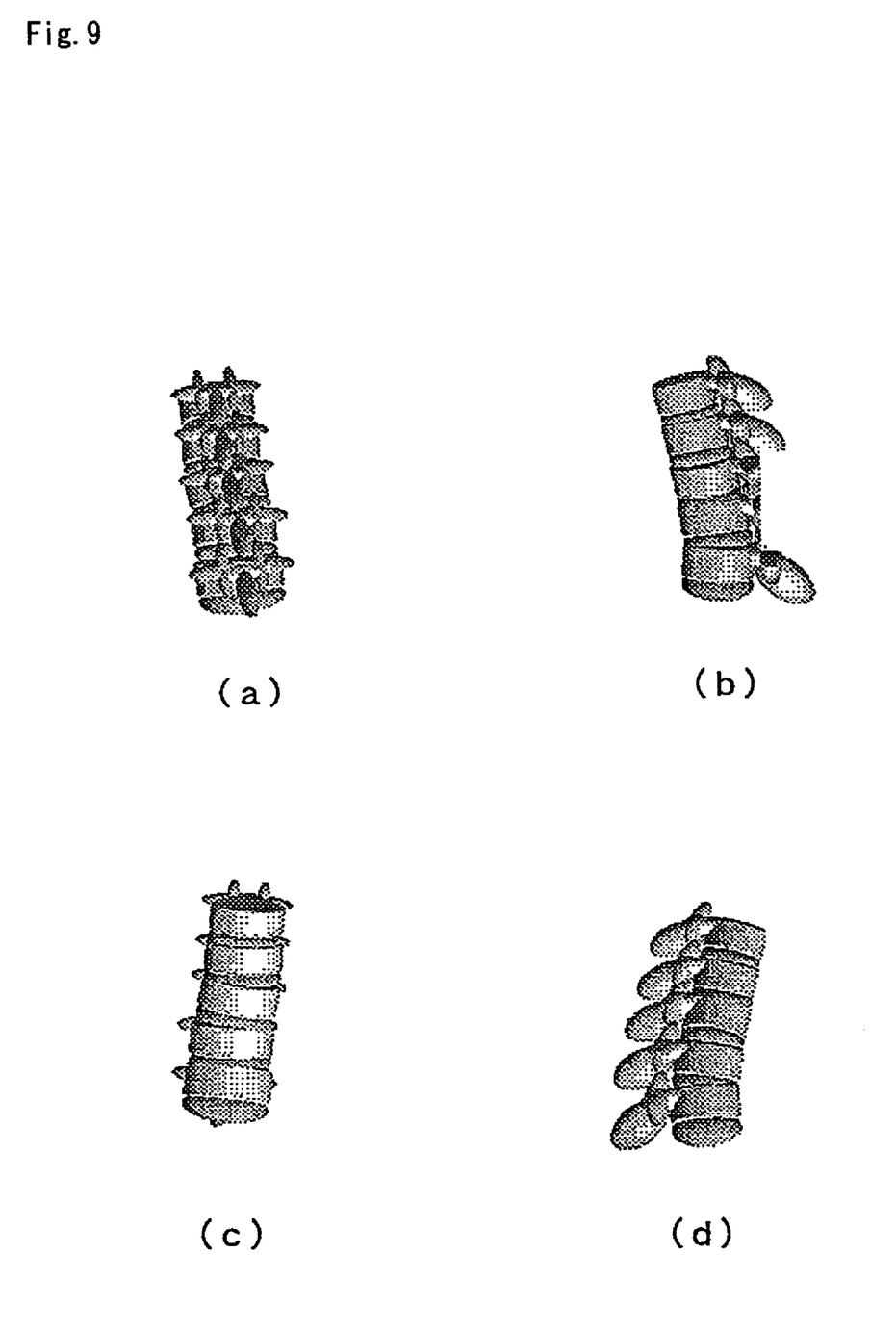
FIG. 9 illustrates explanatory views of images of the spinal column (the upper thoracic vertebrae) displayed by an image display apparatus of the human spinal column measuring and displaying system according to the embodiment of the invention.

FIG. 9 illustrates images of the spinal column generating to display only the superior thoracic vertebrae in the spinal column displayed by FIG. 8, FIG. 9 (a) is an explanatory view generating to display an image of the spinal column on the back side of the superior thoracic vertebrae, FIG. 9 (b) is an explanatory view generating to display an image of the spinal column on the left side of the superior thoracic vertebrae, FIG. 9 (c) is an explanatory view generating to display an image of the spinal column on the front side of the superior thoracic vertebrae and FIG. 9 (d) is an explanatory view generating to display an image of the spinal column on the right side of the superior thoracic vertebrae, respectively.

FIG. 9 (a) is the explanatory view generating to display the image of the spinal column on the back side of the superior thoracic vertebrae, displaying the first thoracic vertebra, the second thoracic vertebra, the third thoracic vertebra and the fourth thoracic vertebra referred to as the superior vertebrae in the thoracic vertebrae and the fifth thoracic vertebra disposed on the lower side of the fourth thoracic vertebra.

Further, along with the image of the superior thoracic vertebrae, a bending angle in front and rear direction and a bending angle in left and right direction may be calculated, for example, with regard to the bending angle in front and back direction, an explanation of the bending angle in front and back direction may be displayed such that the bending angle of the first thoracic vertebra relative to the second thoracic vertebra is 'angle of the first thoracic vertebra→ the second thoracic vertebra=2.85 degrees to the front side', . . . , the bending angle of the fourth thoracic vertebra relative to the fifth thoracic vertebra is 'angle of the fourth thoracic vertebra→the fifth thoracic vertebra=10.86 degrees to the front side'. Similarly, with regard to the bending angle in left and right direction, the bent state of the spinal column may be displayed by displaying an explanation of the bending angle between the thoracic vertebrae such that the bending angle of the first thoracic vertebra relative to the second thoracic vertebra is 'angle of the first thoracic vertebra→the second thoracic vertebra=3.00 degrees to the left', . . . , the bending angle of the fourth thoracic vertebra relative to the thoracic vertebra is 'angle of the fourth thoracic vertebra→the fifth thoracic vertebra=5.40 degrees to the right side'.

Further, in a state of displaying the image of the spinal column on the back side of the superior thoracic vertebrae as shown by FIG. 9 (a), by depressing a predetermined key (for example, 'RIGHT key (→) ' or 'LEFT key (→)') provided at the input apparatus 10, the view point can be changed and an image rotating the currently displayed superior thoracic vertebrae can be displayed.

For example, in a state of displaying the image of the spinal column on the back side of the superior thoracic vertebrae of FIG. 9 (a), when 'LEFT key (←)' is depressed, as shown by FIG. 9 (b), the image of the spinal column on the left side constituted by rotating the back side of the superior thoracic vertebrae in the right direction by 90 degrees is displayed and similar to the above-described, the bending angle in front and back direction and bending angle in left and right direction are calculated to respectively display.

Successively, in a state of displaying the image of the spinal column on the left side of the superior thoracic vertebrae as shown by FIG. 9 (b), by depressing the predetermined key 'LEFT key ←)' provided at the input apparatus 10, as shown by FIG. 9 (c), the image of the spinal column on the front side constituted by rotating the left side of the superior thoracic vertebrae by 90 degrees further in the right direction is displayed and similar to the above-described, the bending angle in front and back direction and the bending angle in left and right direction are respectively displayed and by further depressing 'LEFT key (←)', as shown by FIG. 9 (d), the image of the spinal column on the right side constituted by rotating the front side of the superior thoracic vertebrae by 90 degrees further in the right direction.

Further, in a state of displaying the image of FIG. 8 (a) or FIG. 8 (b), when a predetermined key (for example, 'DOWN key (↓)') provided at the input apparatus 10 is depressed, the display can be switched to display of only the middle thoracic vertebrae and similar to the above-described, the bending angle in front and back direction and the bending angle in left and right direction can be calculated to display such that with regard to the bending angle in front and back direction, the bending angle of the sixth thoracic vertebra relative to the fifth thoracic vertebra is 'angle of the fifth thoracic vertebra→the sixth thoracic vertebra=2.73 degrees to the back side', . . . , the bending angle of the ninth thoracic vertebra relative to the eighth thoracic vertebra is 'angle of the eighth thoracic vertebra↓the ninth thoracic vertebra=7.58 degrees to the front side' and so on.

Further, when 'DOWN key (↓)' is depressed, only the inferior thoracic vertebrae are displayed, further, when 'DOWN key (↓)' is depressed, only the lumbar vertebrae are displayed.

That is, according to the display apparatus main body, by forming the image of the spinal column based on the basic diagram data 15 and the vertebrae data table 16, reflecting bending by the measured data thereto and displaying the vertebrae of the portion by moving coordinates thereof in a predetermined direction, a total or a portion of the spinal column as shown by FIG. 8 or FIG. 9 (a) is displayed on the back side, by depressing the predetermined key, a state of moving the view point by 90 degrees is simulated to display and a pseudo-spinal column such as the spinal column on the left side of FIG. 9 (b), the spinal column on the front side of FIG. 9(c) or the spinal column on the right side of FIG. 9(d) can be displayed.

In this way, it can easily be recognized optically how which vertebra is bent in the plurality of vertebrae constituting the spinal column.

Next, an explanation will be given of a behavior of measuring the state of the spinal column of the human body and three-dimensionally displaying the state by the computer graphics by the human spinal column measuring and displaying system 1 of the invention in reference to flowcharts of FIG. 10 through FIG. 12.

Figure 10:
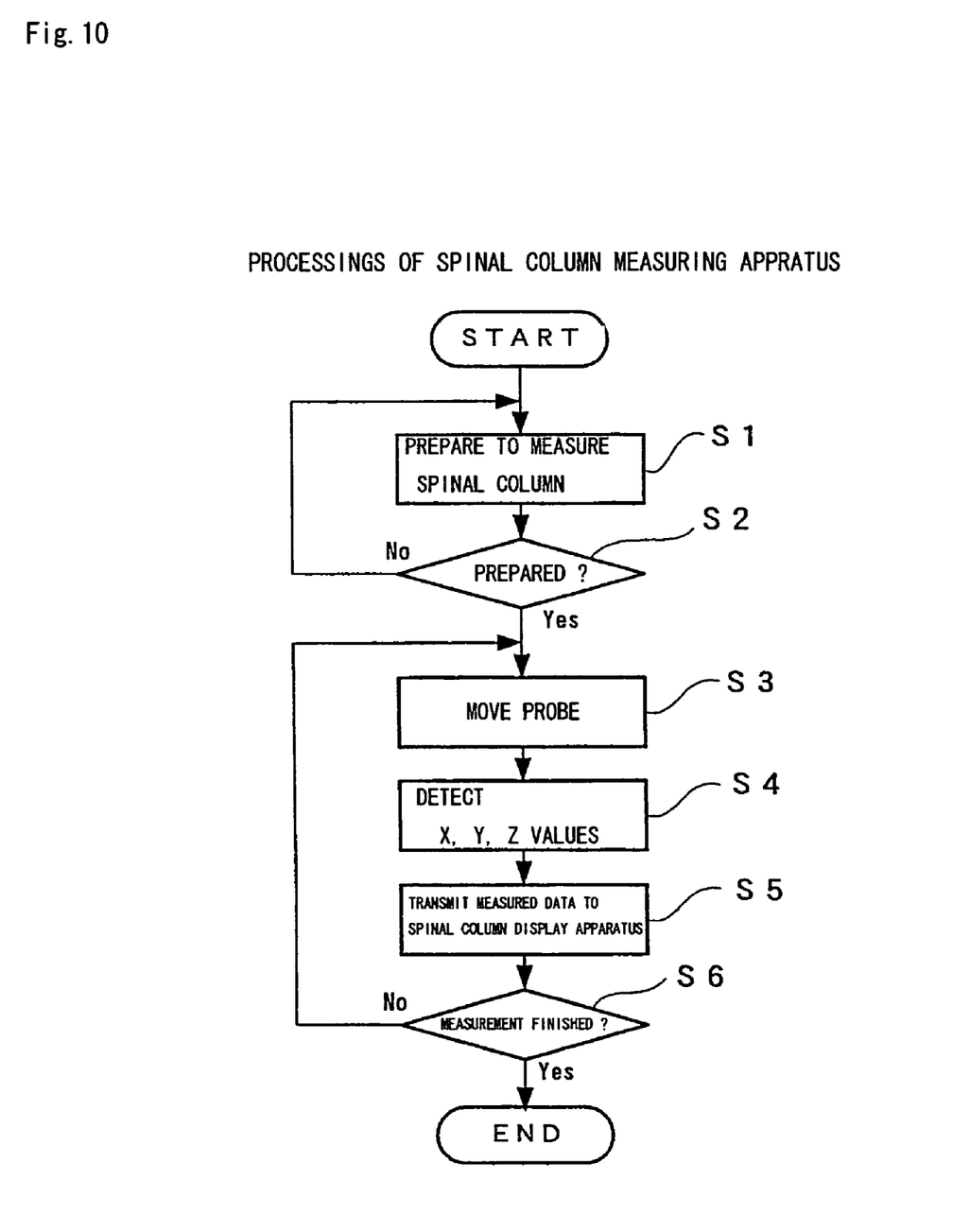
FIG. 10 is a flowchart of a behavior of converting a measured data by the display apparatus main body 2 of the human spinal column measuring and displaying system according to the embodiment of the invention.

FIG. 10 is a flowchart of a behavior of measuring a state of the spinal column of a patient (measured subject).

In order to measure the state of the spinal column of the patient (measured subject), power source is switched on to the measuring and displaying system, the patient (measured subject) is made to lie on one's head to prepare measurement (step S1).

According thereto, preparation is finished when values displayed in the coordinates detecting apparatus 8, for example, X value and Y value become '0' or '1' when the power source is inputted thereto.

Further, it is checked whether the preparation is finished (step S2), when the preparation is not finished, the operation returns to the processing of step S1 to carry out preparation. When the preparation is finished, the measuring person holds the probe 3 by the hand to move to direction of the head of the patient (measured subject) to arrange on the spinal column on the side of the cervical vertebrae of the patient (measured subject) to move along on the spinal column toward the side of the lumbar vertebrae (step S3).

When the probe 3 is moved, recesses and projections and a degree of bending of the spinal column are detected as X value, Y value and Z value (step S4). The detected measured data is transmitted to the display apparatus main body 9 (step S5). Further, it is determined whether the measurement is finished (step S6) and when the measurement is finished, the processings are finished. When the measurement is not finished yet, the operation returns to the processing of step S3 and the probe 3 is moved successively on the spinal column.

Figure 11:
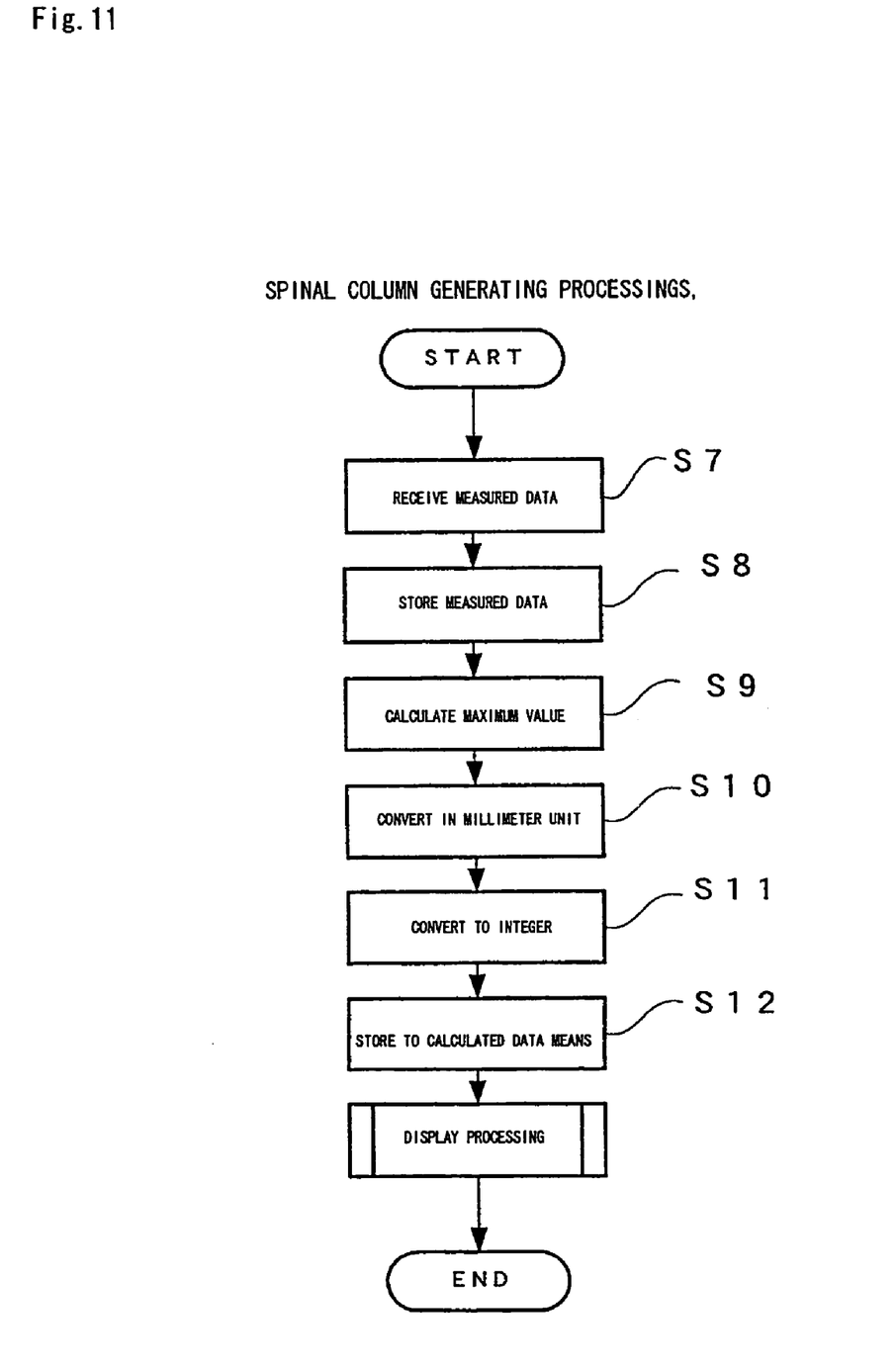
FIG. 11 is a flowchart of a behavior of converting the measured data by the display apparatus main body 2 of the human spinal column measuring and displaying system according to the embodiment of the invention.

FIG. 11 is a flowchart of a behavior of converting the measured data by the display apparatus main body 9.

Successively, receiving the measured data (step S7) the display apparatus main body 9 stores the measured data to the measured data storing means 12 (step S8) and calculates a maximum value from data in which X value of the measured data is equal to or smaller than 1 mm by the converting means 13 (step S9). Since lower first number of the maximum value is below the decimal point and therefore, the decimal point is marked and the data is converted by a unit of mm (Step S10). Here, the value below the decimal point is considered as an error in measurement and therefore, the number below the decimal point of the measured data is rounded off to constitute an integer (step S11). The measured data converted into an integer is stored to the converted data storing means 14 (step S12).

Figure 12:
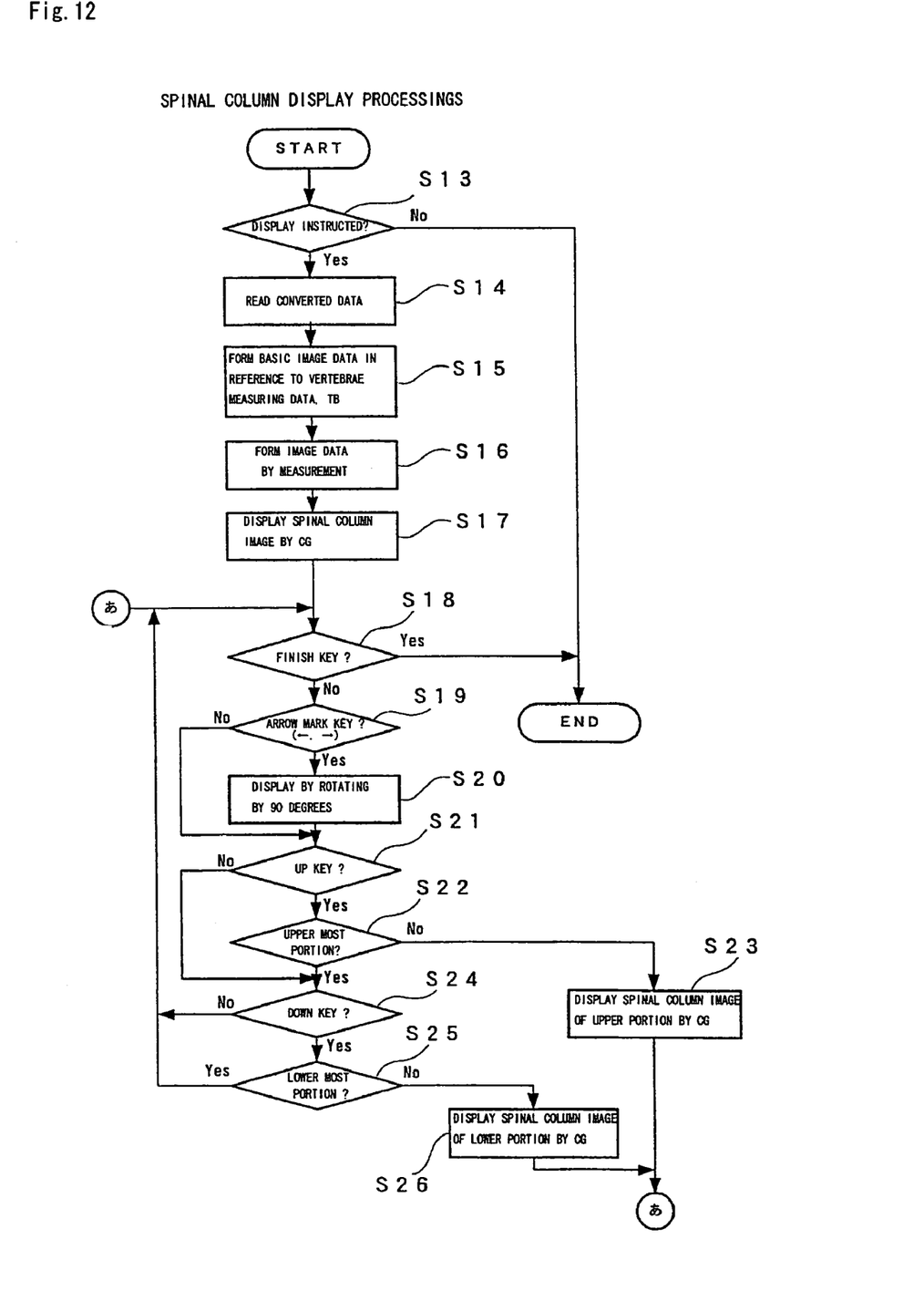
FIG. 12 is a flowchart of a behavior of displaying a bent state of the generated spinal column by using computer graphics based on the measured data of the human spinal column measuring and displaying system according to the embodiment of the invention.

FIG. 12 is a flowchart of a behavior of displaying the bent state of the generated spinal column by using the computer graphics based on the measured data.

In order to display the state of the spinal column by using the computer graphics, predetermined instruction is inputted from the input apparatus 15 of a mouse or the like connected to the spinal column measuring apparatus 2 (step S13) and when instruction is not carried out, the processings are finished.

When display is instructed, the converted data (measured data) is read from the converted data storing means 14 (step S14), the image data of the basic model of the spinal column based on gender and height of the measured subject is formed in reference to the basic diagram data 15 and the vertebrae table 16 based on the image processing software program previously set to the display apparatus main body 9 (step S15), the three-dimensional spinal column image data of the measured subject is generated by reflecting the converted data (measured data) to the three-dimensional spinal column image data of the basic model (step S16) and is displayed on the display screen 11 (step S17).

When the image of the three-dimensional pseudo-spinal column is displayed on the display screen 11, here, it is determined whether the processings are finished (step S18) and when a finish key is depressed, the processings are finished.

Other than optically recognizing bending in left and right direction by displaying the image of the spinal column generated in this way from the back side, the image of the spinal column is displayed from left and right sides such that bending in front and back direction can optically be recognized, when an arrow mark key (→or ←) is depressed (step S19), the image of the spinal column is displayed by moving the view point by 90 degrees in a predetermined direction (step 20), when UP key is depressed (step S21), it is determined whether the upper most portion (the superior thoracic vertebrae portion) is displayed (step S22) and when the upper most portion is displayed, since a further upper side cannot be displayed, a current displayed portion is displayed as it is and in the case in which the upper most potion is not displayed, a portion above the currently displayed portion is displayed (step S23).

Further, when DOWN key is depressed (step S24), it is determined whether the lower most potion (the lumbar vertebrae portion) is displayed (step S25), when the lower most portion is displayed, since a further lower side cannot be displayed, the currently displayed portion is displayed as it is and when the lower most potion is not displayed, a portion below the currently displayed portion is displayed (step S26).

That is, in order to measure to display the bent state of the spinal column by utilizing the human spinal column measuring and displaying system 1 of the invention, gender and height of the patient (measured subject) are needed, further, a state before treatment (symptom of the neck, the shoulder, the back, the waist or the like) is provided by diagnosis by question or description of a preparatory diagnosis leaf.

Further, the state of the spinal column is measured as described above and displayed on the display screen 11 by the three-dimensional computer graphics.

An explanation is given to the patient (measured subject) while letting the patient see the displayed image of the spinal column and a treatment is carried out of the spinal column of a portion which is bent in comparison with the normal state. When the treatment is finished, the state of the spinal column is measured again and the pseudo-spinal column is displayed on the display screen 11 by the three-dimensional computer graphics.

Further, the states of the spinal column before treatment and after treatment can be seen to compare by the images displayed on the display screen 11 or the images outputted to print.

By displaying the bent state of the spinal column before treatment and after treatment by the pseudo-spinal column images, both of the physician and the patient (measured subject) can easily be informed of the bent state of the spinal column.

Further, although according to the embodiment, an explanation has been given by constituting the probe by the inverse-T like shape, the shape is not particularly limited so far as the probe can be scanned above the spinal column.

Further, although according to the embodiment, an explanation has been given such that the image of the vertebrae is generated by reading correspondent data from the basic diagram data and the vertebrae table in order to constitute the image of the vertebrae of the measured subject, the image of the vertebrae in correspondence with height and gender of the measured subject may be provided as a data base and so far as the vertebrae of each measured subject can be displayed, a style or a storing method of data for visualizing the vertebrae to form the image is not particularly limited.

Further, although according to the embodiment, an explanation has been given such that an image of the spinal column is displayed by the three-dimensional computer graphics and the view point is moved by 90 degrees, the view point may be moved by 45 degrees and a range of moving the view point is not particularly limited.

Industrial Applicability

As has been explained above, according to the human spinal column measuring and displaying system of the invention, in what state the spinal column is bent can optically be recognized by the pseudo-three dimensional image by the simple and convenient method of scanning the probe on the surface above the spinal column of the measured subject who lies on one's face.

Thereby, there is achieved an advantage that the physician can easily give explanation by explaining how much is the degree of bending the spinal column before treatment and after treatment in reference to the image.

Further, the patient who is the measured subject can easily understand how and in which way which portion of the spinal column of one's own is bent since the state of the spinal column similar to the actual spinal column can optically be recognized not by specialized medical terminology but as the image.

The invention claimed is:

1. A human spinal column measuring and displaying system comprising:

a probe provided at a front end of a scanning arm movable in a longitudinal X-axis direction, a width Y-axis direction and a thickness Z-axis direction of the spinal column of a measured subject and pinched between the second finger and the third finger of a measuring person for detecting detaching amounts from reference positions in the X, the Y and the Z axes-directions by three-dimensionally moving front ends of the fingers from a position of the first cervical vertebra or a position of the first thoracic vertebra to a position of the fifth lumbar vertebra of the spinal column of the measured subject;

converted data storing means for storing respective values of measured data in the X-axis direction, the Y-axis direction and the Z-axis direction of the detaching amounts detected by the probe;

an input apparatus for inputting a gender and a height of the measured subject;

a readable medium comprising basic diagram data stored with an average size and a basic shape of each of the vertebrae constituting the spinal column of the human body by the gender and the height of the measured subject;

a readable medium comprising a table of the vertebrae for selecting each of the vertebrae in correspondence with the gender and the height from the basic diagram data in accordance with the gender and the height of the measured subject inputted by the input apparatus;

synthesizing means for generating an image of a total of the spinal column constituting a basic image based on a size and a shape of each of the vertebrae selected by using the table of the vertebrae; and image data generating means for generating a three-dimensional image of the spinal column of the measured subject at positions of coordinates in the X direction, the Y direction and the Z direction of each of the vertebrae on the basic image of the spinal column generated by the synthesizing means based on the measured data stored to the converted data storing means to display the three-dimensional image of the spinal column on a display screen.

2. The human spinal column measuring and displaying system according to claim 1, wherein the three-dimensional image of the spinal column is displayed by moving the image of the spinal column displayed on the display screen in a predetermined direction or rotating the image by a predetermined angle based on a predetermined instruction.

* * * * *